US00PP14568P29

(12) United States Plant Patent
Kaagman

(10) Patent No.: US PP14,568 P2
(45) Date of Patent: Feb. 24, 2004

(54) DAHLIA PLANT NAMED 'DADA YELLOW'

(50) Latin Name: *Dahlia variabilis*
Varietal Denomination: Dada Yellow

(75) Inventor: Pim Kaagman, Andijk (NL)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 10/404,826

(22) Filed: Apr. 1, 2003

(51) Int. Cl.[7] ..... A01H 5/00
(52) U.S. Cl. ..... Plt./321
(58) Field of Search ..... Plt./321

*Primary Examiner*—Bruce R. Campell
*Assistant Examiner*—A Para
(74) *Attorney, Agent, or Firm*—Jondle & Associates PC

(57) ABSTRACT

A dahlia cultivar particularly distinguished by yellow colored flowers, compact habit and good basal branching.

1 Drawing Sheet

Genus and species: *Dahlia variabilis.*
Variety denomination: 'Dada Yellow'.

BACKGROUND OF THE NEW PLANT

The present invention comprises a new and distinct cultivar of dahlia, botanically known as *Dahlia variabilis*, and hereinafter referred to by the cultivar name 'Dada Yellow'. The new cultivar is asexually reproduced from vegetative cuttings and tissue culture resulting from the cross of the seed/pod parent Dahlstar Salmon (U.S. Plant Pat. No. 12,750)×DA-93, a yellow proprietary line that is unnamed and unpatented.

'Dada Yellow' is a product of a planned breeding program intended to create new dahlia plants with yellow colored flowers, compact habit, good basal branching and moderately vigorous growth.

The new cultivar was created in 1997 in Andijk, The Netherlands and has been asexually reproduced repeatedly by vegetative cuttings and tissue culture in Gilroy, Calif., Andijk, The Netherlands, and Guatemala over a four-year period. The plant has also been trialed at Gilroy, Calif., Litchfield, Mich. and Andijk, The Netherlands. The present invention has been found to retain its distinctive characteristics through successive propagations; and this novelty is firmly fixed.

DESCRIPTION OF PHOTOGRAPH

This new petunia plant is illustrated by the accompanying photograph which shows blooms, buds, and foliage of the plant in full color, the colors shown being as true as can be reasonably obtained by conventional photographic procedures.

The photograph shows the mature inflorescence.

DESCRIPTION OF THE NEW CULTIVAR

The following detailed descriptions set forth the distinctive characteristics of 'Dada Yellow'. The data, which defines these characteristics, were collected from asexual reproductions carried out in Gilroy, Calif. The plant history was taken on 10 months old plants grown in one-gallon pots in fall/winter season, in a poly-covered greenhouse under 2–4 hours supplemental light and color readings were taken in the greenhouse in the winter season under natural light.

Plants had been cut back numerous times prior to data readings taken. Color references are primarily to The R.H.S. Colour Chart of The Royal Horticultural Society of London (R.H.S.). Texture description details were observed under a dissecting microscope according to The New Royal Horticultural Society Dictionary of Gardening (1992).

Classification:
- *Botanical.*—*Dahlia variabilis.*
- *Commercial.*—Dahlia.

Growth:
- *Form.*—Upright, compact and mounding.
- *Growth and branching habit.*—Good vigorous habit, well branched, full plant.
- *Height.*—From soil level to top of blooms: Approximately 20–30 cm.
- *Width.*—Approximately 40–45 cm including flowers.
- *Time to produce a finished flowering plant.*—9–12 weeks.
- *Outdoor plant performance.*—Fast cropping, free flowering, used in patio planters and mixed container plantings or garden beds.
- *Time to initiate roots.*—Approximately 14–28 days in the greenhouse.
- *Root description.*—Fibrous, white.

Leaves:
- *Arrangement.*—Young foliage leaves are single and mature leaves simple or occasionally compound and trifoliate, opposite.
- *Length.*—6.2–6.7 cm.
- *Width.*—6.5–6.8 cm.
- *Leaf blade shape.*—Elliptic.
- *Leaf margin.*—Dentate/Ciliate.
- *Apex aspect.*—Acute.
- *Base aspect.*—Attenuate.
- *Leaf color.*—Upper surface, close to RHS 147A (yellow-green) and Lower surface, close to RHS 191A (greyed-green) with RHS 138A (green) veins.
- *Texture.*—Strigulose on veins.
- *Venation.*—Pinnate.
- *Venation color.*—RHS 144B (yellow-green).
- *Petiole length.*—2.3–2.5 cm.
- *Petiole width.*—0.2 cm.
- *Petiole color.*—RHS 144B (yellow-green).
- *Petiole texture.*—Slightly hispid.

Stem:

*Length.*—20–25 cm.

*Diameter.*—0.4–0.5 cm.

*Internodes length.*—0.5–0.6 cm.

*Color.*—Between RHS 144A and B (yellow-green).

*Texture.*—Slightly hispid.

*Stem anthocyanin.*—No.

*Peduncle color.*—RHS 144A (yellow-green).

*Peduncle length.*—2.3–3.5 cm.

*Peduncle diameter.*—0.15 cm.

*Peduncle texture.*—Smooth.

Bud:

*Shape.*—Orbicular.

*Diameter.*—1.0–1.4 cm.

*Length.*—1.0–1.2 cm.

*Color at tight bud.*—RHS# 1A (green-yellow) but a little lighter.

Flower:

*Blooming habit.*—Continuous all through the growing season. Good floriferousness.

*Inflorescence type.*—Borne on terminals above foliage, semi-double flowers, floret faces upward or outward.

*Flower diameter.*—4.0–4.5 cm.

*Ray petal color.*—Front side, RHS 1B (green-yellow) and backside, RHS 1B (green-yellow) but a little lighter. Petal length — 2.0–2.2 cm. Petal width — 0.9–1.0 cm. Petal apex shape — Mucronulate. Petal base shape — Attenuate. Petal margin — Entire. Petal texture — Upper side, papillose and underside, slightly pilose on veins mainly. Petal quantity — 58–64.

*Disc petal color.*—RHS 17A (yellow-orange). Petal length — 0.9–1.0 cm. Petal diameter — 0.1–0.15 cm. Petal shape — Elongated, cylindrical, shiny. Petal quantity — 35–40.

*Involucral bracts.*—Usually 5.

*Color.*—RHS 191A (greyed-green) base color with RHS 137A (green) striations.

*Length.*—0.9–1.0 cm.

*Width.*—0.4–0.5 cm.

*Shape.*—Elliptic.

*Apex.*—Acute.

*Texture.*—Slightly Strigulose.

*Lastingness of individual blooms.*—7–12 days.

*Fragrance.*—No.

Reproductive organs:

*Androecium, pollen color.*—RHS 17A (yellow-orange).

*Gynoecium, stigma color.*—RHS 17A (yellow).

*Style color.*—RHS 4D (yellow).

*Pistil length.*—1.3–1.5 cm.

*Fruit seed set.*—Not observed.

Disease and insect resistance: Not observed.

COMPARISON WITH KNOWN CULTIVARS

'Dada Yellow' differs from the female parent 'Dahlstar Salmon' in the following ways: The female parent is salmon-yellow and 'Dada Yellow' is yellow. The female parent is less vigorous than 'Dada Yellow'.

'Dada Yellow' differs from the male parent DA-93 in the following ways: The male parent is a regular size dahlia and 'Dada Yellow' is a dwarf/compact size. The male parent also is a larger flower and the plant is less vigorous.

I claim:

1. A new and distinct dahlia plant as shown and described herein.

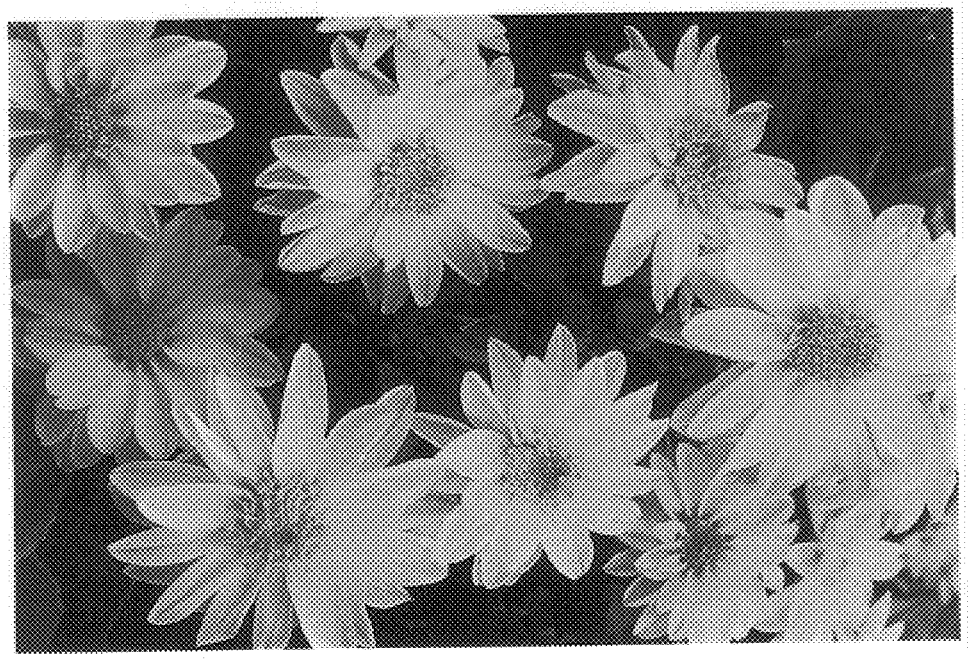

* * * * *